United States Patent
Swanson

(10) Patent No.: US 8,463,403 B2
(45) Date of Patent: Jun. 11, 2013

(54) SPINAL CORD STIMULATION PADDLE LEAD AND METHOD OF MAKING THE SAME

(71) Applicant: Advanced Neuromodulation Systems, Inc., Plano, TX (US)

(72) Inventor: John Swanson, Lake Oswego, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 13/708,263

(22) Filed: Dec. 7, 2012

(65) Prior Publication Data

US 2013/0096662 A1   Apr. 18, 2013

Related U.S. Application Data

(62) Division of application No. 13/238,993, filed on Sep. 21, 2011, now Pat. No. 8,332,048, which is a division of application No. 11/740,507, filed on Apr. 26, 2007, now Pat. No. 8,099,172.

(60) Provisional application No. 60/745,882, filed on Apr. 28, 2006.

(51) Int. Cl.
*A61N 1/05* (2006.01)

(52) U.S. Cl.
USPC .................................. 607/117; 607/116

(58) Field of Classification Search
USPC .................................. 607/117, 116
See application file for complete search history.

(56) References Cited

U.S. PATENT DOCUMENTS

| | | | |
|---|---|---|---|
| 4,658,836 | A | 4/1987 | Turner |
| 5,000,194 | A | 3/1991 | van den Honert et al. |
| 5,158,537 | A | 10/1992 | Haak et al. |
| 5,800,500 | A | 9/1998 | Spelman et al. |
| 5,810,725 | A | 9/1998 | Sugihara et al. |
| 6,024,702 | A | 2/2000 | Iversen |
| 6,151,519 | A | 11/2000 | Sugihara et al. |
| 6,205,361 | B1 | 3/2001 | Kuzma et al. |
| 6,374,143 | B1 | 4/2002 | Berrang et al. |
| 6,415,187 | B1 | 7/2002 | Kuzma et al. |
| 6,522,932 | B1 | 2/2003 | Kuzma et al. |
| 6,624,510 | B1 | 9/2003 | Chan et al. |
| 6,678,564 | B2 | 1/2004 | Ketterl et al. |
| 6,719,582 | B1 | 4/2004 | Swanson |
| 6,757,970 | B1 | 7/2004 | Kuzma et al. |

(Continued)

FOREIGN PATENT DOCUMENTS

| EP | 1818074 | 8/2007 |
|---|---|---|
| WO | WO 2005092432 | 10/2005 |

OTHER PUBLICATIONS

European Patent Office, European Search Report for EP 07250537 dated May 16, 2007.

(Continued)

*Primary Examiner* — Joseph Stoklosa

(57) ABSTRACT

In one embodiment, a method of fabricating an implantable stimulation paddle comprises: providing a sheet of conductive material coupled to a first insulative layer; laser removing portions of the conductive material to form a pattern of conductive material, the pattern of conductive material including a plurality of isolated metal traces; providing a second insulative layer over the pattern of conductive material so that the pattern of conductive material is interposed between the first and second insulative layers; and exposing portions of the metal traces to form electrodes on the paddle for delivering electrical stimulation.

2 Claims, 4 Drawing Sheets

U.S. PATENT DOCUMENTS

| | | |
|---|---|---|
| 6,782,619 B2 | 8/2004 | Corbett et al. |
| 6,895,283 B2 | 5/2005 | Erickson et al. |
| 6,919,633 B2 | 7/2005 | Perlov et al. |
| 6,976,998 B2 | 12/2005 | Rizzo et al. |
| 7,047,084 B2 | 5/2006 | Erickson et al. |
| 7,085,605 B2 | 8/2006 | Bluger et al. |
| 7,107,097 B2 | 9/2006 | Stern et al. |
| 7,107,104 B2 | 9/2006 | Keravel et al. |
| 7,177,702 B2 | 2/2007 | Wallace et al. |
| 7,437,197 B2 | 10/2008 | Harris et al. |
| 7,620,246 B2 | 11/2009 | Akahori |
| 7,697,995 B2 | 4/2010 | Cross et al. |
| 8,099,172 B2 | 1/2012 | Swanson |
| 8,332,048 B2 | 12/2012 | Swanson |
| 2002/0022873 A1 | 2/2002 | Erickson et al. |
| 2002/0111661 A1 | 8/2002 | Cross et al. |
| 2003/0040785 A1 | 2/2003 | Maschino et al. |
| 2003/0158588 A1 | 8/2003 | Rizzo et al. |
| 2003/0204228 A1 | 10/2003 | Cross et al. |
| 2004/0022440 A1 | 2/2004 | Akahori |
| 2004/0243205 A1 | 12/2004 | Keravel et al. |
| 2004/0260310 A1 | 12/2004 | Harris |
| 2005/0070972 A1 | 3/2005 | Wahlstrand et al. |
| 2005/0090885 A1 | 4/2005 | Harris et al. |
| 2005/0154435 A1 | 7/2005 | Stern et al. |
| 2005/0203602 A1 | 9/2005 | Wallace et al. |
| 2005/0288758 A1 | 12/2005 | Jones et al. |
| 2007/0027514 A1 | 2/2007 | Gerber |
| 2007/0265691 A1 | 11/2007 | Swanson |
| 2008/0009929 A1 | 1/2008 | Harris et al. |

OTHER PUBLICATIONS

European Patent Office, International Search Report for PCT/US2007/067642 dated Oct. 12, 2007.

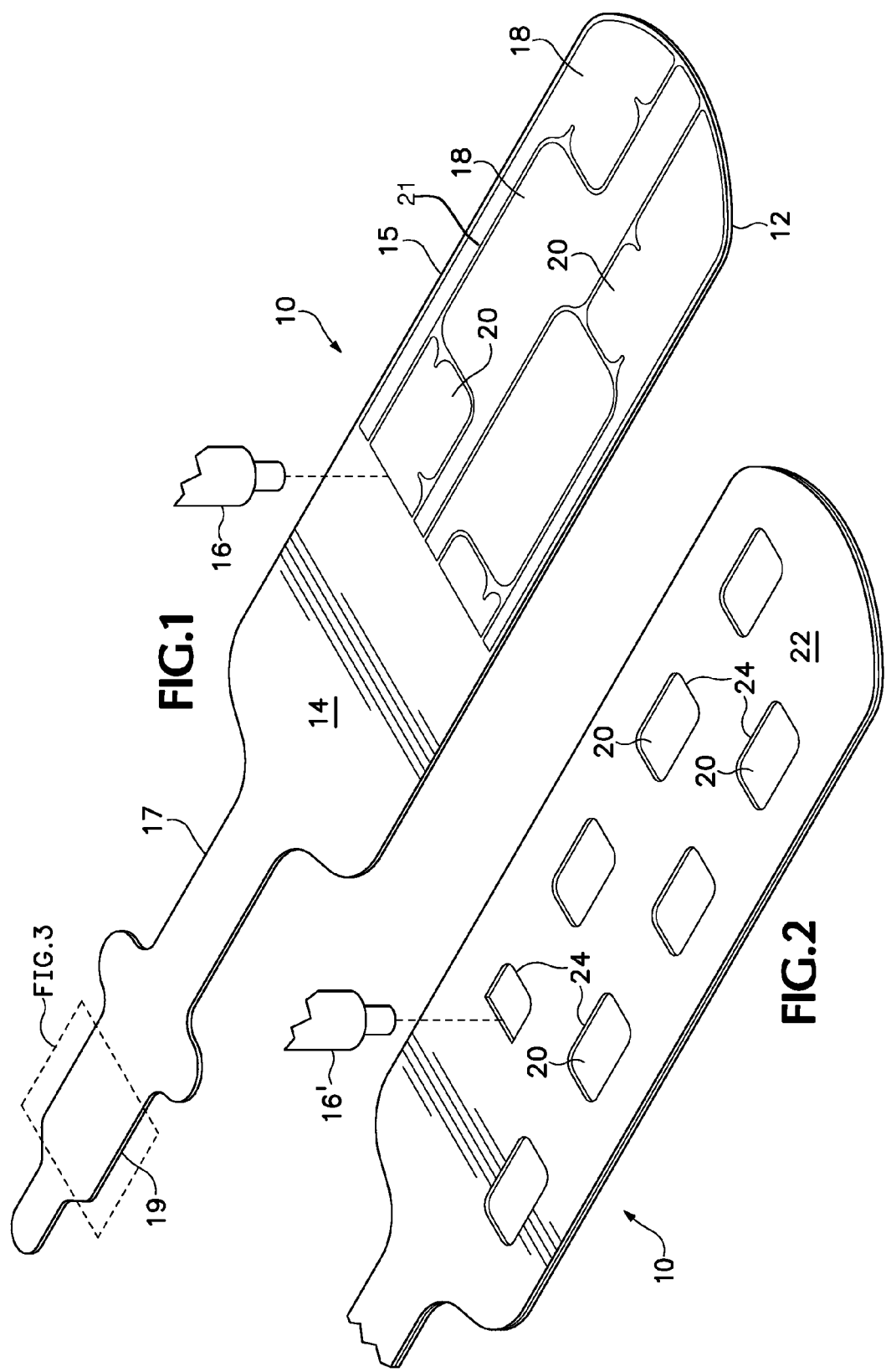

SPINAL CORD STIMULATION PADDLE LEAD AND METHOD OF MAKING THE SAME

RELATED APPLICATION

This application is a continuation of U.S. application Ser. No. 13/238,993, filed Sep. 21, 2011, now U.S. Pat. No. 8,332,048, which is a divisional of U.S. application Ser. No. 11/740,507, filed Apr. 26, 2007, now U.S. Pat. No. 8,099,172, which claims the benefit of U.S. Provisional Application No. 60/745,882, filed Apr. 28, 2006, the disclosures of which are fully incorporated herein by reference for all purposes.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems typically include a pulse generator and one or several leads. The pulse generator is the device that generates the electrical pulses. The pulse generator is typically implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the appropriate nerve tissue.

Stimulation paddle leads dispose a plurality of electrodes (for example, two, four, eight, or sixteen) arranged in one or more columns on a paddle structure. It is typical that implanted SCS paddles are transversely centered over the physiological midline of a patient. In such position, multiple columns of electrodes are well suited to address both unilateral and bilateral pain. A multi-column SCS paddle also enables reliable positioning of a plurality of electrodes that does not deviate over time. In particular, the probability of migration of an SCS paddle after implantation is significantly lower than the probability of migration of percutaneous leads. Additionally, SCS paddles are capable of being sutured in place.

However, given the dimensions of conventional SCS paddles, a surgical procedure is necessary for implantation. The surgical procedure (a "partial laminectomy") requires the resection and removal of certain vertebral structures to allow both access to the dura and proper positioning of the SCS paddle. The invasive nature of the surgical procedure requires some amount of time for patient recovery and, in some cases, could cause long-term complications for the patient. Additionally, due to the relatively complicated nature of the surgical procedure, the procedure is typically performed by a neurosurgeon.

Additionally, it is noted that typical assembly procedures for electrically coupling a lead body to a paddle structure are not only cumbersome and expensive, but also create a number of natural, easy breakage points. Specifically, conventional couplings between lead bodies and paddle structures involve welding a jumper wire between contacts and conductive wires of the lead body. Accordingly, conventional paddle lead fabrication methods may involve undue expense and lower than desired manufacturing yields.

SUMMARY

In one embodiment, a method of fabricating an implantable stimulation paddle comprises: providing a sheet of conductive material coupled to a first insulative layer; laser removing portions of the conductive material to form a pattern of conductive material, the pattern of conductive material including a plurality of isolated metal traces; providing a second insulative layer over the pattern of conductive material so that the pattern of conductive material is interposed between the first and second insulative layers; and exposing portions of the metal traces to form electrodes on the paddle for delivering electrical stimulation.

In another embodiment, an implantable medical lead for delivering electrical energy to stimulate a patient comprises: a lead body comprising a plurality of helically wound conductive wires embedded in insulative material; and a paddle comprising a metal layer disposed between insulative layers, wherein a plurality of electrically isolated metal traces are patterned in the metal layer, each metal trace comprises an electrode exposed through one or several insulative layers, and each electrode is electrically coupled to a conductive wire of the lead body.

In another embodiment, a system for electrically stimulating a patient comprises: an implantable pulse generator (IPG) for generating electrical stimulation; a lead body comprising a plurality of helically wound conductive wires, embedded in insulative material, for conducting electrical stimulation from the IPG; and a paddle comprising a metal layer disposed between insulative layers, wherein a plurality of electrically isolated metal traces are patterned in the metal layer, each metal trace comprises an electrode exposed through one or several insulative layers, and each electrode is electrically coupled to a conductive wire of the lead body.

In another embodiment, a method comprises: providing a lead body having a plurality of conductive wires, wherein the plurality of conductive wires are helically wound at a wire spacing pitch; providing a stimulation paddle, the stimulation paddle comprising a metal layer between insulative layers, wherein a plurality of electrically isolated metal traces are patterned in the metal layer, each metal trace comprises a contact and an electrode exposed through one or several insulative layers, and the contacts of the metal traces are disposed together on the stimulation paddle and spaced according to the wire spacing pitch; placing the lead body in contact with the stimulation paddle such that an exposed segment of the lead body abuts the contacts of the metal traces; and transmitting energy onto each contact so that the respective contact becomes welded to an abutting conductive wire of the medical lead thereby electrically coupling the abutting conductive wire to a respective electrode of the stimulation paddle.

The foregoing has outlined rather broadly certain features and/or technical advantages in order that the detailed description that follows may be better understood. Additional features and/or advantages will be described hereinafter. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 1 is an expanded top perspective view of a stimulation paddle shaped work piece, at an early stage in the production process.

FIG. 2 is an expanded top perspective view of a of the work piece of FIG. 1, at a further stage in the production process.

DETAILED DESCRIPTION

Figure 3:
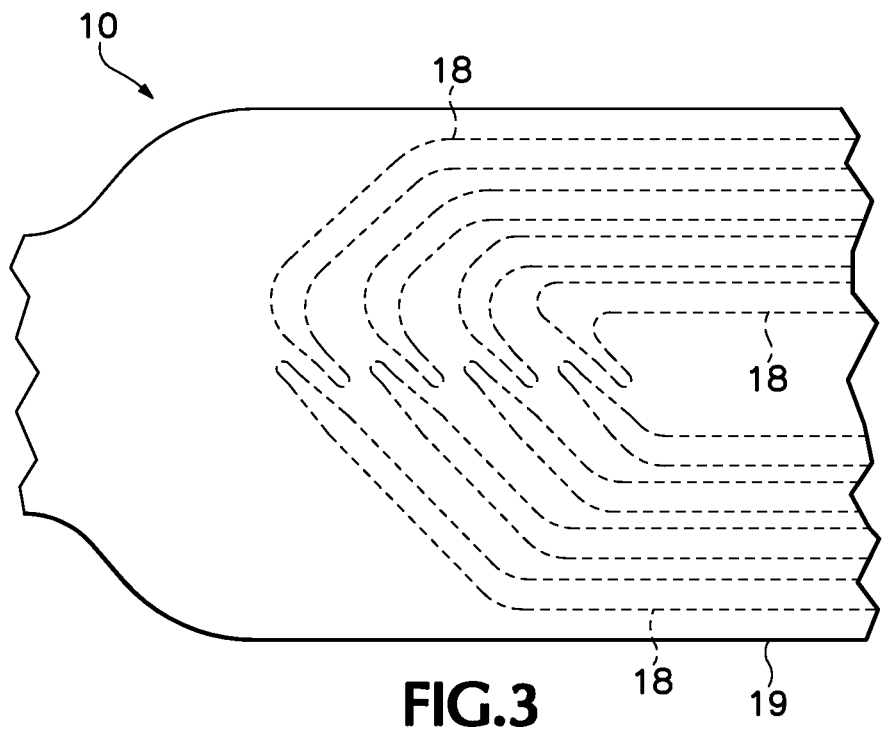
FIG. 3 is an expanded top view of a connector portion of the work piece of FIG. 1, as indicated by the rectangle marked "FIG. 3" in FIG. 2.

One preferred embodiment takes the form of a method of making a spinal cord stimulation lead in the form of a paddle for stimulation of tissue (e.g., an "SCS paddle"). Referring to FIG. 1, in a preferred method, an SCS paddle work piece 10 begins to take form as a thin layer of nervous-tissue-compatible conductive metal 14 adhered or otherwise coupled to a layer of nervous-tissue-compatible dielectric material 12. The shape of the work piece 10 can be described as including a body 15, a neck 17 and a head 19.

Laser 16 is used to create a set of traces 18 (not completed in FIG. 1) by forming separating trenches 21 in metal layer 14. Sufficient power is applied by laser 16 to ablate a small portion of the metal layer 14 preferably without ablating through the layer of dielectric material 12. Once completed, each trace 18 is electrically isolated from each other trace 18. Also, each trace 18 joins an electrode site 20 in body 15 to a device contact 28 (FIG. 4), in the form of a finger, in head 19.

Referring to FIG. 2, an additional layer of nervous-tissue-compatible dielectric material 22 is then added on top of metal layer 14, thereby covering electrode sites 20, traces 18 (FIG. 3) and device contacts 28. A solid film can be adhered to metal layer 14. Additionally or alternatively, a spin coat of insulative material could be applied to metal layer 14. Layer 22 is then patterned with a second laser 16' (adapted for machining dielectric material) to create a set of apertures 24, which reveal the electrode sites 20. In an alternative preferred embodiment, the same laser is used for both removing metal and dielectric material. Also, in alternative embodiments, the electrode sites 20 could be exposed using manual or other mechanical means.

Figure 4:
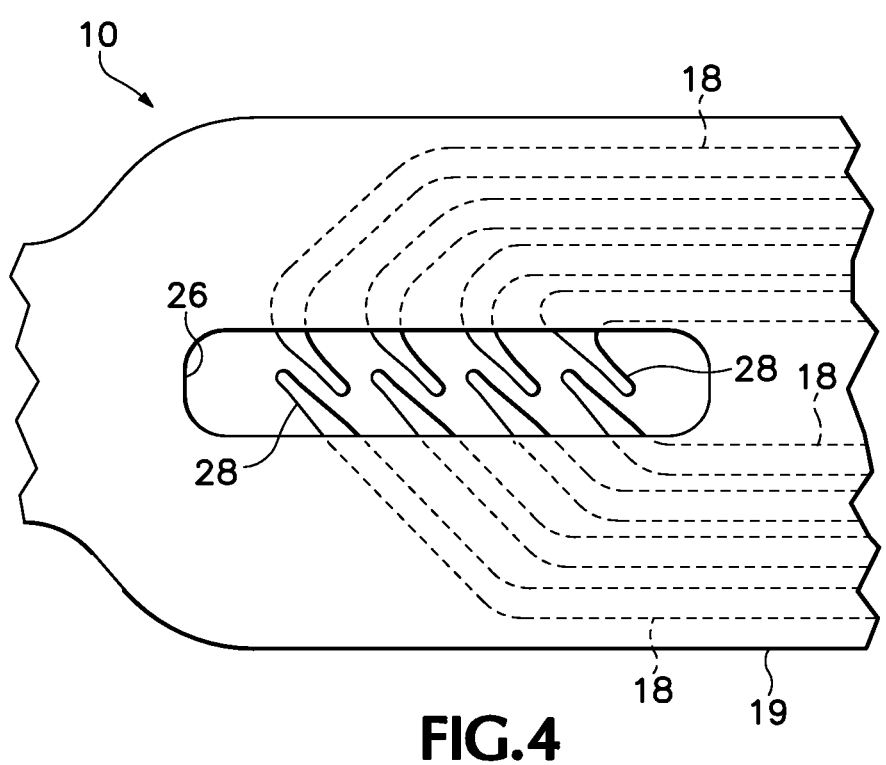
FIG. 4 is an expanded top view of the connector portion of FIG. 3 showing the result of further machining of the work piece of FIG. 1, after removal of a window of dielectric material to expose a portion of the traces, which had been entirely embedded.
Figure 5:
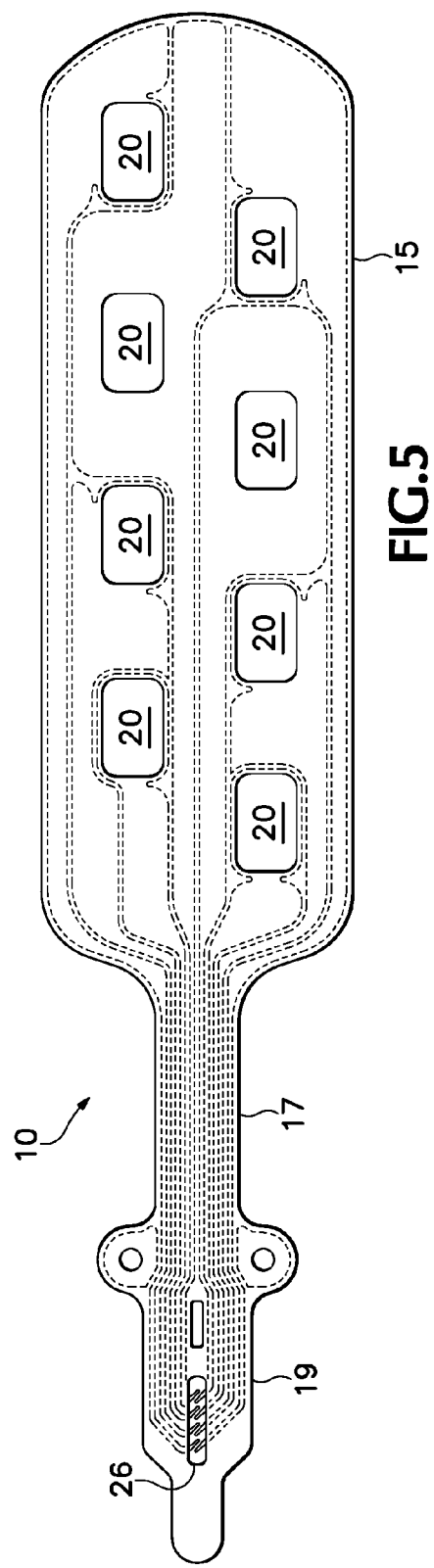
FIG. 5 is a plan view of a completed SCS paddle, resulting from the manufacturing process shown in FIGS. 1 4.
Figure 6:
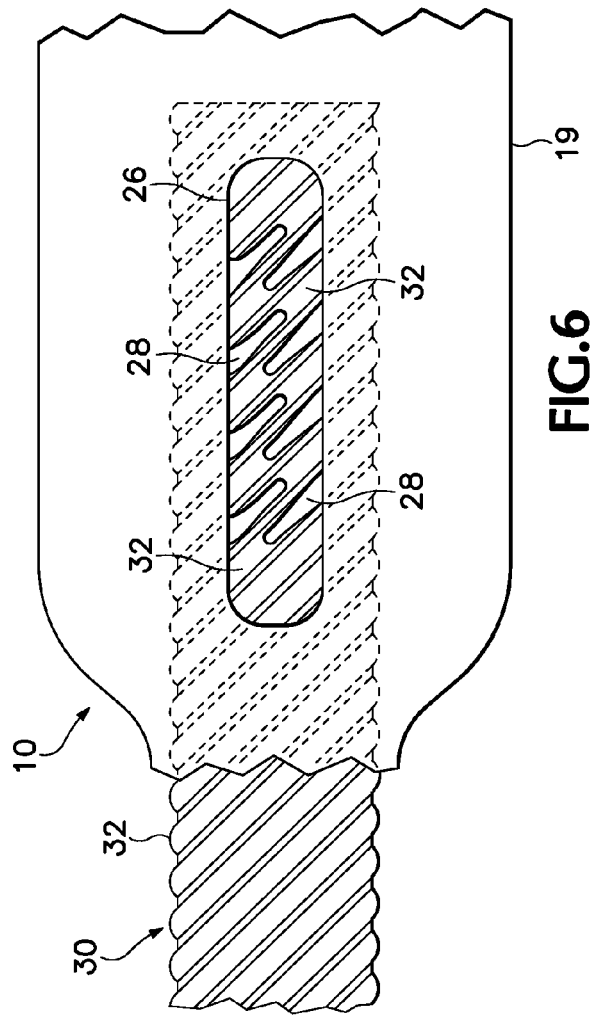
FIG. 6 is an expanded top view of the connector portion of FIG. 5 placed with the window over a portion of a multiconductor cable.

Referring to FIGS. 3 and 4, a window 26 is then created by laser 16', revealing the device electrical contacts 28. The completed SCS paddle 10 is shown in FIG. 5. Referring to FIG. 6, SCS paddle 10 is then placed over a medical lead 30, so that the device electrical contacts 28 are each aligned with and placed over a conductive wire 32 of lead 30. At this point, the insulation of lead 30 has been partially removed to expose conductive wires 32 which are co-located with contacts 28. It shall be appreciated that the relative dimensions of the contacts 28, lead 30, and conductive wires 32 are not depicted to scale in FIG. 6.

Figure 7:
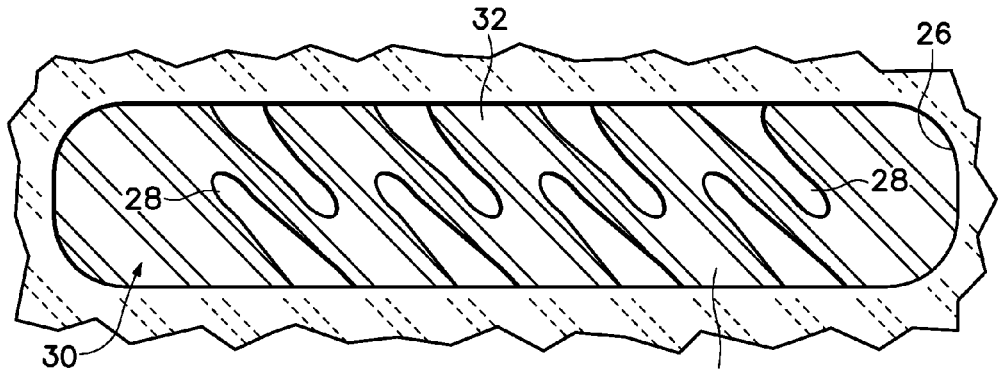
FIG. 7 is an expanded top view of the connector portion and lead body of FIG. 5, showing the exposed traces of the connector portion after being laser welded to the underlying conductive wires of the lead body.

A laser beam, from the first laser 16 (FIG. 1), is then focused so that part of its footprint covers a part of a device electrical contact 28 and/or part covers a portion of the corresponding exposed conductive wire 32. The energy, transmitted quickly, heats device electrical contact 28 and conductive wire 32, melting the end of contact 28 and causing it to be securely welded to conductive wire 32, as shown in FIG. 7. This procedure is repeated for each device electrical contact 28. In an alternative preferred embodiment, each electrical contact 28 is micro-spot welded to conductive wire 32. In this technique a microprobe touches and transmits electrical energy onto the free face of electrical contact 28. As the system is grounded, this causes a large flow of electrical energy, which melts portions of contact 28, welding it to conductive wire 32.

Figure 8:
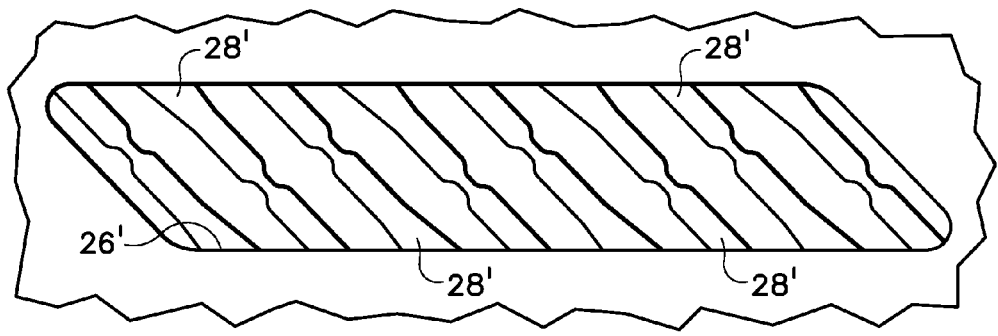
FIG. 8 is an expanded top view of a connector portion of an alternative preferred embodiment of a stimulation paddle work piece, at the same stage of manufacturing as is the work piece of FIG. 4.

FIG. 8 shows the connective portion of an alternative preferred embodiment of a stimulation paddle work piece in which device electrical contacts 28' extend all the way across window 26'. The welding of device electrical contacts 28' to the lead 30 (FIG. 6) may be essentially identical to the welding of device electrical contacts 28 as described above. The preferred embodiment of FIG. 8 may afford a greater stability to device electrical contacts 28', versus device electrical contacts 28, as contacts 28' are anchored on both sides of window 26'.

Figure 9:
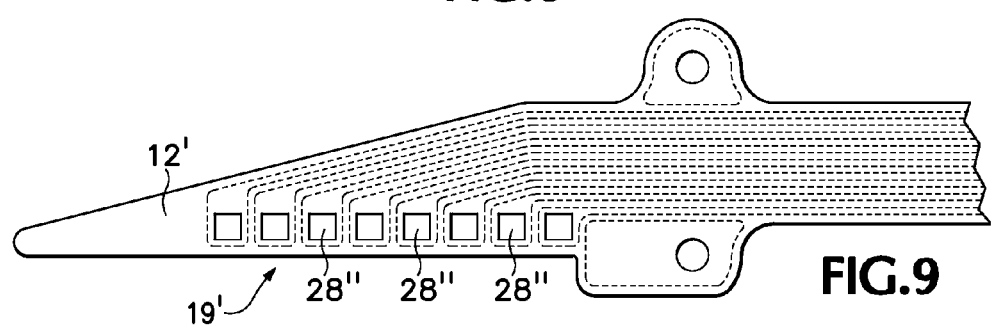
FIG. 9 shows an alternative preferred embodiment of a paddle head having a polymeric coating on the back side of the connection contact sites, which are spaced further apart from each other than in previously shown embodiments.
Figure 10:
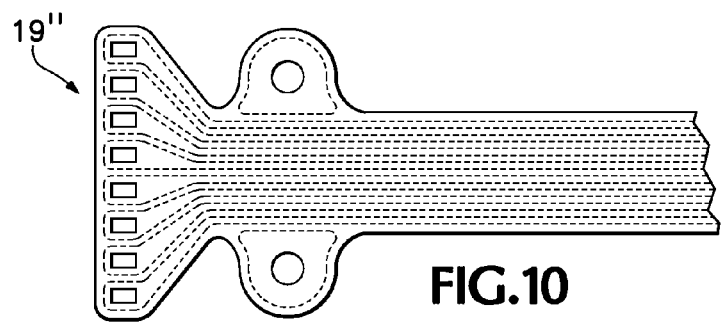
FIG. 10 shows an alternative preferred embodiment of a paddle head that is similar in concept to the paddle of FIG. 9, but is adapted for the case in which the paddle is positioned perpendicular to the lead body.

FIG. 9 shows an alternative preferred embodiment of a head 19' with a polymeric coating 12' on the back side of contact sites 28", which are spaced further apart from each other. In one preferred method the polymeric coating 12' is melted or ablated off by laser 16 (FIG. 1) as contact sites 28" are laser welded to a cable. The head 19" of FIG. 10 is similar in concept to the head of FIG. 9, but is adapted for the case in which the lead is arranged in a manner perpendicular to the cable.

A range of nervous system tissue compatible polymeric materials, sold under the trade designation Bionate® and sold in sheets that may be laminated together are available from Polymer Technology Group of Berkeley, Calif. Metal 14 (FIG. 1) may be gold or a platinum-iridium alloy. First laser 16 may be a ND:YAG laser, which in one preferred embodiment is frequency multiplied, and second laser 16' may be a frequency multiplied ND:YAG laser or a CO2 laser. Conductive wires 32 (FIG. 6) may be made of an alloy that is referred to by the trade designation MP35N and is available from Fort Wayne Metals of Fort Wayne, Ind.

It shall be appreciated that these material selections are by way of example and any other suitable materials could be substituted without departing from the scope of the appended claims. Also, although some embodiments have been discussed in terms of SCS paddles, stimulation paddles for other indications can be fabricated according to other embodiments. For example, stimulation paddles can be fabricated according to some embodiments for cardiac stimulation, cortical stimulation, deep brain stimulation, peripheral nerve stimulation, gastric pacing, etc.

The above described methods of paddle fabrication are quite highly automated; thereby requiring far fewer manual operations compared with previously available production techniques for known stimulation paddles. This potentially lowers the costs of manufacturing and reduces the reject rate. Moreover, the process permits the creation of a set of paddles that are more precisely uniform to one another, thereby permitting a medical professional to have confidence that a particular paddle will not fail over time due to inaccurate fabrication processes.

The disclosed combination of physical dimensions and mechanical characteristics further enables SCS paddles to be inserted within the epidural space of a patient without performing a partial laminectomy. Specifically, by utilizing relatively thin layers of material, SCS paddles can be folded or otherwise deformed for placement within an insertion tool. The insertion tool can be inserted through spacing in the vertebral structures into the epidural space. The SCS paddle is then passed through the end of the insertion tool. The shape memory characteristic of the metal layer and, perhaps, the dielectric backing enables the SCS paddle to resume its original shape upon exiting the insertion tool thereby exposing the electrodes of the paddle to deliver the electrical stimulation.

Additionally, the physical dimensions and mechanical characteristics of the paddle reduce the probability of causing spinal cord compression. In some alternative embodiments, the paddle can also be made thick enough to be retained in place by the compressing force between the vertebrae and the spinal cord.

Skilled persons will appreciate that by using the above described method it is possible to create and connect an electrical probe having features that are on the order of 0.1 $mm^2$ in area without the risk of leaving trace amounts of photolithography agents on the probe. This is particular important in that nervous system tissue is highly sensitive and easily damaged by a wide range of compounds (even in very small concentrations).

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

The invention claimed is:

1. An implantable medical lead for delivering electrical energy to stimulate a patient, comprising:
   a lead body comprising a plurality of helically wound conductive wires embedded in insulative material, the helically wound conductive wires being wound at a wire spacing pitch;
   a paddle comprising a metal layer disposed between insulative layers, wherein a plurality of electrically isolated metal traces are patterned in the metal layer, each metal trace comprises a contact and an electrode exposed through one or several insulative layers, and the contacts of the metal traces are disposed together on the paddle and spaced according to the wire spacing pitch; and
   each electrode being electrically coupled to a conductive wire of the lead body.

2. The implantable medical lead of claim 1 wherein the contacts of the metal traces are welded to conductive wires of the lead body.

* * * * *